(12) United States Patent
Jones et al.

(10) Patent No.: US 7,537,916 B2
(45) Date of Patent: *May 26, 2009

(54) EFFICIENT PRODUCTION OF F(AB')$_2$ FRAGMENTS IN MAMMALIAN CELLS

(75) Inventors: David Halford Ashton Jones, London (GB); Abraham Bout, Moerkapelle (NL)

(73) Assignee: Crucell Holland B.V., Leiden (NL)

( * ) Notice: Subject to any disclaimer, the term of this patent is extended or adjusted under 35 U.S.C. 154(b) by 0 days.

This patent is subject to a terminal disclaimer.

(21) Appl. No.: 12/070,145

(22) Filed: Feb. 14, 2008

(65) Prior Publication Data

US 2008/0166767 A1 Jul. 10, 2008

Related U.S. Application Data

(63) Continuation of application No. 10/499,298, filed as application No. PCT/NL02/00841 on Dec. 17, 2002.

(30) Foreign Application Priority Data

Dec. 17, 2001 (WO) ............... PCT/NL01/00917

(51) Int. Cl.
   *C12N 15/07* (2006.01)
   *C12N 15/13* (2006.01)
   *C12N 5/22* (2006.01)

(52) U.S. Cl. ............... 435/69.6; 435/69.1; 435/70.1; 435/70.3

(58) Field of Classification Search ............... None
   See application file for complete search history.

(56) References Cited

U.S. PATENT DOCUMENTS 4,624,846 A * 11/1986 Goldenberg ............... 424/1.49
5,122,458 A 6/1992 Post et al.
5,168,062 A 12/1992 Stinski
5,591,828 A 1/1997 Bosslet et al.
5,648,237 A 7/1997 Carter
5,994,128 A 11/1999 Fallaux et al.

FOREIGN PATENT DOCUMENTS

| EP | 1108787 | 6/2001 |
|---|---|---|
| EP | 1130099 | 9/2001 |
| WO | WO 93/06217 | 4/1993 |
| WO | WO 00 63403 | 10/2000 |
| WO | WO 01/38362 A2 | 5/2001 |
| WO | WO 03/051927 A2 | 6/2003 |

OTHER PUBLICATIONS

PCT International Search Report, PCT/NL02/00841, dated Aug. 20, 2003.
PCT International Preliminary Examination Report, PCT/NL02/00841 dated Apr. 14, 2004.
Leung et al., Abstract, The effects of domain deletion, glycosylation, and long IgG3 hinge on the biodistribution and serum stability properties of a humanized IgG1 immunoglobulin, hLL2, and its fragments, Clin Cancer Res., Oct. 1999, pp. 3106s-3117s, Suppl. 10.
Boshart et al., Abstract, A very strong enhancer is located upstream of an immediate early gene of human cytomegalovirus, Cell, Jun. 1985, pp. 521-530, vol. 2.
Fallaux et al., Abstract, New helper cells and matched early region 1-deleted adenovirus vectors prevent generation of replication-competent adenoviruses, Hum Gene Ther., Sep. 1998, pp. 1909-1917, vol. 9, No. 13.

* cited by examiner

*Primary Examiner*—Q. Janice Li
*Assistant Examiner*—Kevin K. Hill
(74) *Attorney, Agent, or Firm*—TraskBritt

(57) ABSTRACT

The present invention provides immortalized eukaryotic cells and methods useful for the production of immunologically active bivalent antibody fragments, such as F(ab')$_2$ fragments. The methods and cells of the invention result in a desirable ratio of bivalent to monovalent antibody fragments.

9 Claims, 9 Drawing Sheets

```
ATGGCATGCCCTGGCTTCCTGTGGGCACTTGTGATCTCCACCTGTCTTGAATTTTCC
ATGGCTGAAATTGAGCTCACCCAGTCTCCATCCTCCCTGTCTGCATCTGTAGGAGAC
AGAGTCACCATCACTTGCCGGGCAAGTCAGAGCATTAGCAGCTATTTAAATTGGTAT
CAGCAGAAACCAGGGAAAGCCCCTAAGCTCCTGATCTATGCTGCATCCAGTTTACAA
AGTGGGGTCCCATCAAGGTTCAGTGGCAGTGGATCTGGGACAGATTTCACTCTCACC
ATCAGCAGTCTGCAACCTGAAGATTTTGCAACTTACTACTGTCAGCAGAGGAGGGCT
ATGCCTACGAAGTTCGGCGGAGGGACCAAGGTGGAGATCAAACGTAAGTGCACTTTG
CGGCCGCTAGGAAGAAACTCAAAACATCAAGATTTTAAATACGCTTCTTGGTCTCCT
TGCTATAATTATCTGGGATAAGCATGCTGTTTTCTGTCTGTCCCTAACATGCCCTGT
GATTATCCGCAAACAACACACCCAAGGGCAGAACTTTGTTACTTAAACACCATCCTG
TTTGCTTCTTTCCTCAGGAACTGTGGCTGCACCATCTGTCTTCATCTTCCCGCCATC
TGATGAGCAGTTGAAATCTGGAACTGCCTCTGTTGTGTGCCTGCTGAATAACTTCTA
TCCCAGAGAGGCCAAAGTACAGTGGAAGGTGGATAACGCCCTCCAATCGGGTAACTC
CCAGGAGAGTGTCACAGAGCAGGACAGCAAGGACAGCACCTACAGCCTCAGCAGCAC
CCTGACGCTGAGCAAAGCAGACTACGAGAAACACAAAGTCTACGCCTGCGAAGTCAC
CCATCAGGGCCTGAGCTCGCCCGTCACAAAGAGCTTCAACAGGGGAGAGTGTTAG
(SEQ ID NO:7)
```

FIG. 8

```
ATGGCATGCCCTGGCTTCCTGTGGGCACTTGTGATCTCCACCTGTCTTGAATTTTCC
ATGGCCGAGGTGCAGCTGGTGGAGTCTGGGGGAGGCTTGGTACAGCCTGGGGGGTCC
CTGAGACTCTCCTGTGCAGCCTCTGGATTCACCTTTAGCAGCTATGCCATGAGCTGG
GTCCGCCAGGCTCCAGGGAAGGGGCTGGAGTGGGTCTCAGCTATTAGTGGCAGTGGT
GGTAGCACATACTACGCAGACTCCGTGAAGGGCCGGTTCACCATCTCCAGAGACAAT
TCCAAGAACACGCTGTATCTGCAAATGAACAGCCTGAGGGCCGAGGACACGGCCGTG
TATTACTGTGCAAGAGACGACCGGCCTAGGGAGTTGGACTCCTGGGGCCAAGGTACC
CTGGTCACCGTCTCGACAGGTGAGTGCGGCCGCGAGCCCAGACACTGGACGCTGAAC
CTCGCGGACAGTTAAGAACCCAGGGGCCTCTGCGCCCTGGGCCCAGCTCTGTCCCAC
ACCGCGGTCACATGGCACCACCTCTCTTGCAGCCTCCACCAAGGGCCCATCGGTCTT
CCCCCTGGCACCCTCCTCCAAGAGCACCTCTGGGGGCACAGCGGCCCTGGGCTGCCT
GGTCAAGGACTACTTCCCCGAACCGGTGACGGTGTCGTGGAACTCAGGCGCCCTGAC
CAGCGGCGTGCACACCTTCCCGGCTGTCCTACAGTCCTCAGGACTCTACTCCCTCAG
CAGCGTGGTGACCGTGCCCTCCAGCAGCTTGGGCACCCAGACCTACATCTGCAACGT
GAATCACAAGCCCAGCAACACCAAGGTGGACAAGAGAGTTGGTGAGAGGCCAGCACA
GGGAGGGAGGGTGTCTGCTGGAAGCCAGGCTCAGCGCTCCTGCCTGGACGCATCCCG
GCTATGCAGTCCCAGTCCAGGGCAGCAAGGCAGGCCCCGTCTGCCTCTTCACCCGGA
GGCCTCTGCCCGCCCCACTCATGCTCAGGGAGAGGGTCTTCTGGCTTTTTCCCCAGG
CTCTGGGCAGGCACAGGCTAGGTGCCCCTAACCCAGGCCCTGCACACAAAGGGGCAG
GTGCTGGGCTCAGACCTGCCAAGAGCCATATCCGGGAGGACCCTGCCCCTGACCTAA
GCCCACCCCAAAGGCCAAACTCTCCACTCCCTCAGCTCGGACACCTTCTCTCCTCCC
AGATTCCAGTAACTCCCAATCTTCTCTCTGCAGAGCCCAAATCTTGTGACAAAACTC
ACACATGCCCACCGTGCCCAGGTAAGCCAGCCCAGGCCTCGCCCTCCAGCTCAAGGC
GGGACAGGTGCCCTAGAGTAGCCTGCATCCAGGGACAGGCCCCAGCCGGGTGCTGAC
ACGTCCACCTCCATCTCTTCCTCAGCACCTGAACTCCTGGGGGGACCGTCAGTCTTC
CTCTTCCCCCCAAAACCCAAGGACACCCTCATGATCTCCCGGACCCCTGAGGTCACA
TGCGTGGTGGTGGACGTGAGCCACGAAGACCCTGAGGTCAAGTTCAACTGGTACGTG
GACGGCGTGGAGGTGCATAATGCCAAGACAAAGCCGCGGGAGGAGCAGTACAACAGC
ACGTACCGTGTGGTCAGCGTCCTCACCGTCCTGCACCAGGACTGGCTGAATGGCAAG
GAGTACAAGTGCAAGGTCTCCAACAAAGCCCTCCCAGCCCCCATCGAGAAAACCATC
TCCAAAGCCAAAGGTGGGACCCGTGGGGTGCGAGGGCCACATGGACAGAGGCCGGCT
CGGCCCACCCTCTGCCCTGAGAGTGACCGCTGTACCAACCTCTGTCCCTACAGGGCA
GCCCCGAGAACCACAGGTGTACACCCTGCCCCCATCCCGGGAGGAGATGACCAAGAA
CCAGGTCAGCCTGACCTGCCTGGTCAAAGGCTTCTATCCCAGCGACATCGCCGTGGA
GTGGGAGAGCAATGGGCAGCCGGAGAACAACTACAAGACCACGCCTCCCGTGCTGGA
CTCCGACGGCTCCTTCTTCCTCTATAGCAAGCTCACCGTGGACAAGAGCAGGTGGCA
GCAGGGGAACGTCTTCTCATGCTCCGTGATGCATGAGGCTCTGCACAACCACTACAC
GCAGAAGAGCCTCTCCCTGTCCCCGGGTAAATGA   (SEQ ID NO:8)
```

FIG. 9

```
ATGGCATGCCCTGGCTTCCTGTGGGCACTTGTGATCTCCACCTGTCTTGAATTTTCC
ATGGCCGAGGTGCAGCTGGTGGAGTCTGGGGGAGGCTTGGTACAGCCTGGGGGGTCC
CTGAGACTCTCCTGTGCAGCCTCTGGATTCACCTTTAGCAGCTATGCCATGAGCTGG
GTCCGCCAGGCTCCAGGGAAGGGGCTGGAGTGGGTCTCAGCTATTAGTGGCAGTGGT
GGTAGCACATACTACGCAGACTCCGTGAAGGGCCGGTTCACCATCTCCAGAGACAAT
TCCAAGAACACGCTGTATCTGCAAATGAACAGCCTGAGGGCCGAGGACACGGCCGTG
TATTACTGTGCAAGAGACGACCGGCCTAGGGAGTTGGACTCCTGGGGCCAAGGTACC
CTGGTCACCGTCTCGACAGGTGAGTGCGGCCGCGAGCCCAGACACTGGACGCTGAAC
CTCGCGGACAGTTAAGAACCCAGGGGCCTCTGCGCCCTGGGCCCAGCTCTGTCCCAC
ACCGCGGTCACATGGCACCACCTCTCTTGCAGCCTCCACCAAGGGCCCATCGGTCTT
CCCCCTGGCACCCTCCTCCAAGAGCACCTCTGGGGGCACAGCGGCCCTGGGCTGCCT
GGTCAAGGACTACTTCCCCGAACCGGTGACGGTGTCGTGGAACTCAGGCGCCCTGAC
CAGCGGCGTGCACACCTTCCCGGCTGTCCTACAGTCCTCAGGACTCTACTCCCTCAG
CAGCGTGGTGACCGTGCCCTCCAGCAGCTTGGGCACCCAGACCTACATCTGCAACGT
GAATCACAAGCCCAGCAACACCAAGGTGGACAAGAGAGTTGGTGAGAGGCCAGCACA
GGGAGGGAGGGTGTCTGCTGGAAGCCAGGCTCAGCGCTCCTGCCTGGACGCATCCCG
GCTATGCAGTCCCAGTCCAGGGCAGCAAGGCAGGCCCCGTCTGCCTCTTCACCCGGA
GGCCTCTGCCCGCCCCACTCATGCTCAGGGAGAGGGTCTTCTGGCTTTTTCCCCAGG
CTCTGGGCAGGCACAGGCTAGGTGCCCCTAACCCAGGCCCTGCACACAAAGGGGCAG
GTGCTGGGCTCAGACCTGCCAAGAGCCATATCCGGGAGGACCCTGCCCCTGACCTAA
GCCCACCCCAAAGGCCAAACTCTCCACTCCCTCAGCTCGGACACCTTCTCTCCTCCC
AGATTCCAGTAACTCCCAATCTTCTCTCTGCAGAGCCCAAATCTTGTGACAAAACTC
ACACATGCCCACCGTGCCCACATCATCACCATCACCATTGA
```

(SEQ ID NO:9)

FIG. 10

EFFICIENT PRODUCTION OF F(AB')₂ FRAGMENTS IN MAMMALIAN CELLS

CROSS-REFERENCE TO RELATED APPLICATIONS

This application is a continuation of application Ser. No. 10/499,298, filed Oct. 25, 2004, pending, which is a national stage entry under 35 U.S.C. § 371 of International Patent Application No. PCT/NL02/00841, filed Dec. 17, 2002, published in English as International publication WO 03/051927 A2 on Jun. 26, 2003, which claims the benefit under 35 U.S.C. § 119 of International Patent Application No. PCT/NL01/00917, filed Dec. 17, 2001, the contents of all of which are incorporated herein by this reference in their entireties.

TECHNICAL FIELD

The invention relates generally to biotechnology, and, more particularly, to recombinant protein production, e.g., to production of immunologically active antibody fragments in eukaryotic cells, such as F(ab')$_2$ fragments in eukaryotic cells.

BACKGROUND OF THE INVENTION

Results of recent clinical trials have generated much excitement and optimism for the potential benefits of fully human antibodies in the diagnosis and treatment of disease. This success is in part due to the technology of selecting antibodies against novel targets from phage display libraries and also due to improved production platforms.

One IgG molecule comprises two heavy chains and two light chains. The heavy chains consist of (starting from the N-terminus): a variable region, a constant region, a hinge region and two additional constant regions (FIG. 1). The hinge region contains cysteine residues that form disulphide bonds with a second heavy chain to mediate dimerization of the protein. The number of cysteine residues varies depending on the IgG sub-class: IgG1 has 2 cysteines that form disulphide bonds in the hinge. The light chains consist of a variable region and a constant region; residues C-terminal to the constant region form disulphide bonds with residues immediately before the heavy chain hinge regions. Thus the four chains are held together by multiple disulphide bonds as well as other noncovalent interactions between the intimately paired chains.

The structure of an antibody may be defined as distinct domains: the Fc region which mediates effector functions and the F(ab') region which binds antigen (George and Urch, 2000). The two C-terminal constant domains of the heavy chains make up the Fc region. A F(ab') fragment comprises the light chain and the variable and first constant region of the heavy chain; a F(ab')$_2$ fragment comprises two F(ab') fragments dimerized through the heavy chain hinge region (FIG. 1).

Antibodies are under investigation as therapies for a wide range of clinical problems including organ transplantation, cardiac disease, infectious diseases, cancer, rheumatologic and autoimmune disease, neurologic disorders, respiratory diseases, as well as disorders with organs such as the blood, skin and digestive tract.

One of the major focuses for antibody discovery and development is in the field of cancer imaging and therapy (Carter, 2001). Antibodies may be used as naked molecules or they may be labeled and so used as a magic bullet to deliver a cargo to the tumor (Borrebaeck and Carlsson, 2001; Park and Smolen, 2001). A number of naked antibodies are currently in the clinic. While it is clear that they are able to reduce tumor load in patients, the mechanism by which this occurs is unclear. Classically, these might work by recruiting effector cells (via Fc receptors) or complement to the target cell. More recently, it is becoming apparent that they may also function by binding cell surface proteins and then activating inappropriate signaling pathways or apoptotic signaling pathways, leading to cell death (Tutt et al., 1998).

Antibodies are currently used in the clinic, both as intact IgG molecules and as F(ab') and F(ab')2 fragments. When choosing an antibody format, there are several important issues. They should have a high antigen avidity and specificity, be sufficiently small to penetrate tumor tissue and remain in the circulation long enough to localize to tumors. In addition (particularly if they are labeled with a radiolabel or other toxic moiety), they should be cleared from the body at a rate which prevents non-specific toxicity or high background.

F(ab')$_2$ fragments exhibit a number of benefits over intact IgG related to the above points, which make them attractive for imaging and therapy. First, these molecules have a shorter half-life than an intact IgG, because they are more rapidly removed from the circulation by the kidneys as a result of their lower molecular weight, thus reducing potential toxicity (Behr et al., 1995). Another advantage of the reduced size is that they may penetrate tumor tissue and associated vasculature more readily (Yokota et al, 1992). In this way, more cells of the tumor mass are targeted.

Advantages also exist due to the absence of the Fc region of the molecule. The F(ab')$_2$ fragment does not induce activation of immune responses, as the Fc region (which binds complement and Fc receptors) is absent. This is of particular relevance in imaging studies where only a snapshot of tumor dispersion and size is required. F(ab')$_2$ fragments also do not have the problem of non-specific binding to targets through the Fc moiety, reducing background and non-specific labeling. The advantages listed above may also apply in part to F(ab') fragments. However, F(ab')$_2$ molecules are bivalent (as are intact IgGs) and so should bind target molecules with higher avidity. F(ab') fragments are monovalent and, as a result, generally exhibit lower avidities. For these reasons, F(ab')$_2$ fragments are highly desirable as clinical agents.

While advantages of F(ab')$_2$ fragments are clear, it has not proven as easy to make F(ab')$_2$ fragments. Several methods are currently available. The classic method is to make intact IgG, digest it with a protease, such as pepsin, to remove the Fc region of the antibody. Other regions of the molecule may, however, be nicked by the protease (including the antigen-binding region, resulting in the loss of binding capacity of the antigen-binding region) and digestion may not be complete. Further purification is then required to remove the F(ab')$_2$ fragment from the non-digested antibody, the free Fc domain and the protease.

An alternative method is to make F(ab') fragments in bacteria and then dimerize the molecules to generate F(ab')$_2$ molecules (Willuda et al., 2001; Zapata et al., 1995; Humphreys et al., 1998; U.S. Pat. No. 5,648,237). Dimerization may use specific self-associating peptides (which may prove antigenic in vivo), conjugation via chemical cross-linkers or in vitro reduction/oxidation of F(ab')-hinge fragments. These methods require additional purification steps and may produce unusual molecules (such as two F(ab') fragments linked "head-to-tail" so that the antigen-binding regions are at opposite ends of the new molecule).

Another method for producing F(ab')$_2$ fragments is to generate them directly in mammalian cells. While this might appear straightforward, it has been observed that F(ab') fragments are often produced in preference to F(ab')$_2$ fragments.

One report in which CHO cells were used for IgG4 F(ab')$_2$ production indicated that F(ab')$_2$ fragments accounted for only 10% of the protein produced, with F(ab') fragments accounting for 90% (King et al., 1992; King et al., 1994). The reason for this is unclear. Another important cell line in the production of monoclonal antibodies is SP2/0; an attempt to produce IgG1 F(ab')$_2$ fragments in this cell line yielded essentially only monovalent products. Addition of an IgG3 hinge, which comprises 11 sulfur bridges instead of the two sulfur bridges present in an IgG1 hinge, resulted in the production of 98% divalent product (Leung et al., 1999). However, increased numbers of sulfur bridges generally decreases production levels of the antibody fragments and it is, therefore, preferable to have fewer sulfur bridges for production on a large scale. A similar picture was seen upon expression of F(ab')$_2$ fragments in COS cells (De Sutter et al., 1992). Thus, despite these efforts, there is still a need for improved production methods of F(ab')$_2$ fragments. PER.C6™ is a human cell line and an example of an immortalized primary eukaryotic host cell. It is able to grow in suspension culture in serum-free medium, which, upon transfection with an appropriate expression vector and selection of stable cell lines, is capable of producing recombinant protein in abundance, as disclosed in WO 00/63403. In the '403 application, it has been disclosed that PER.C6™ cells can express intact human IgG, but no specific data have been provided for F(ab')$_2$ fragments.

SUMMARY OF THE INVENTION

PER.C6™ cells, as an example of eukaryotic immortalized primary cells, are capable of more efficiently producing and secreting F(ab')$_2$ fragments without the need to take the special measures of the prior art. The F(ab')$_2$ fragment so produced and secreted can bind antigen as efficiently as intact IgG, while the monovalent F(ab') binds considerably less efficiently.

More in particular, the cell line PER.C6™ and derivatives thereof, appear to be very suitable for the production of bivalent fragments of Ig-molecules and wherein the monovalent moieties making up the bivalent Ig-molecule fragment are linked via one or more disulphide bonds. Thus, an immortalized primary eukaryotic host cell is provided comprising nucleic acid encoding an immunologically active bivalent multimeric antibody fragment, and/or a precursor thereof, functionally linked to sequences capable of driving expression of the fragments in the host cell when the cell is cultured under conditions allowing expression.

Provided is a host cell comprising adenovirus E1 sequences and further comprising recombinant nucleic acid encoding an immunologically active bivalent multimeric antibody fragment, and/or a precursor thereof, functionally linked to one or more sequences capable of driving expression of the fragment in the host cell. In certain embodiments, the immunologically active bivalent multimeric antibody fragment comprises a F(ab')$_2$ fragment. The host cell is preferably a eukaryotic cell, more preferably, a mammalian cell and, even more preferably, a human cell. In certain embodiments, a host cell according to the invention is derived from a retina cell, preferably a retina cell from a human embryo. In certain embodiments, the host cell is obtainable from a host cell chosen from the group consisting of 293 and PER.C6™ cells or progeny thereof. The host cell provided is obtainable from a PER.C6™ cell. The host cell may comprise a nucleic acid sequence encoding at least one E1 protein of an adenovirus or a homologue, fragment and/or derivative thereof, wherein the homologue, fragment and/or derivative thereof is functional in immortalizing a primary cell when expressed in the cell. Also provided is a PER.C6™ cell comprising a nucleic acid encoding a F(ab')$_2$ fragment. In certain embodiments, the sequence driving expression comprises a region from a CMV promoter and, preferably, the region of the CMV promoter comprises the CMV immediate early gene enhancer/promoter from nucleotide −735 to +95. In certain embodiments, the immunologically active bivalent multimeric antibody fragment is capable of selectively binding to activated vitronectin.

Also provided is a host cell expressing and secreting immunologically active bivalent and monovalent antibody fragments, and/or precursors thereof, wherein the ratio of secreted bivalent active antibody fragment to monovalent active antibody fragment by the host cell is at least 1:3, wherein the two antigen-binding regions of the bivalent active antibody fragment are not linked by peptide bonds.

Also provided is a method of making a host cell capable of producing an immunologically active bivalent multimeric antibody fragment, the method comprising: introducing into an immortalized primary eukaryotic cell a nucleic acid sequence comprising a sequence encoding the antibody fragment or precursor thereof operably linked to a sequence capable of driving expression of the sequence encoding the antibody fragments in the cell.

Also provided is a method of producing an immunologically active bivalent antibody fragment, wherein the method comprises culturing a host cell according to the invention. In one aspect, the method further comprises isolating and/or purifying the immunologically active bivalent antibody fragment.

Further provided is a method of producing an immunologically active bivalent antibody fragment, wherein the two antigen-binding regions of the immunologically active bivalent antibody fragment are not linked by a peptide bond, the method comprising: a) providing a host cell comprising adenovirus E1 sequences, the host cell further comprising a recombinant nucleic acid sequence comprising a sequence encoding the antibody fragment or precursor thereof operably linked to a sequence capable of driving expression of the sequence encoding the antibody fragment in the host cell; b) culturing the host cell, so that the antibody fragment is secreted from the host cell, wherein the ratio of secretion of immunologically active bivalent to immunologically active monovalent antibody fragment is at least 1:3.

Also provided is a method of producing an immunologically active bivalent antibody fragment, wherein the two antigen-binding regions of the immunologically active bivalent antibody fragment are not linked by a peptide bond, wherein the method comprises: a) introducing into an immortalized primary eukaryotic host cell a nucleic acid sequence comprising a sequence encoding the antibody fragment or precursor thereof operably linked to a sequence capable of driving expression of the sequence encoding the antibody fragment in the host cell; b) culturing the host cell, whereby the antibody fragment is secreted from the host cell, wherein the ratio of secretion of immunologically active bivalent to immunologically active monovalent antibody fragments is at least 1:3. According to another aspect, the method further comprises: c) isolating and/or purifying the immunologically active antibody fragment. In the certain methods, the two antigen-binding regions of the immunologically active bivalent antibody fragment preferably are linked by one to ten sulfur bridges, more preferably, by one or two sulfur bridges. In certain aspects, the region of the immunologically active bivalent antibody fragment that is linked by the sulfur bridges is not derived from an IgG3. In certain methods, the immunologically active bivalent antibody fragment preferably comprises a F(ab')$_2$ fragment.

According to other embodiments, the host cell is a mammalian cell, more preferably a human cell. In other embodiments, the host cell is derived from a retina cell. In other embodiments, the host cell is chosen from 293 and PER.C6™.

In certain embodiments, the ratio of secretion of immunologically active bivalent to immunologically active monovalent antibody fragments is at least 1:1, more preferably, at least 2:1, and still more preferably, at least 3:1. The host cell according to the method herein may comprise a sequence encoding at least one E1 protein of an adenovirus or a functional homologue, fragment and/or derivative thereof. In yet another embodiment of the method, an immunologically active bivalent antibody fragment is capable of selectively binding to activated vitronectin.

Also provided is a method for obtaining F(ab')$_2$ fragments, the method comprising: a) introducing into a eukaryotic cell a nucleic acid sequence encoding the fragment, or precursor thereof, operably linked to sequences capable of driving expression of the sequence encoding the fragment in the cell; b) culturing the cell, such that the fragment is secreted from the cell, wherein the ratio of secretion of F(ab')$_2$ to F(ab') fragments is at least 1:3; and c) isolating and/or purifying the F(ab')$_2$ fragment; wherein the method is essentially devoid of a protease step.

In certain embodiments, the immunologically active antibody fragment comprises an amino acid sequence that is derived from or immunologically similar to an amino acid sequence for a type of antibody fragment of the species from which the mammalian cell is obtained or derived. The produced antibody fragment can be post-translationally modified according to the modification pattern of the species, thereby allowing for a type of modification that is similar to the "natural" situation. Preferably, the species is a human. It has been observed that, particularly for human and other human-like species such as monkeys, the ratio of produced (human or human-like) dimeric versus monomeric antibody fragment is particularly favorable when the immunologically active antibody fragment comprises an amino acid sequence that is derived from, or immunologically similar to, an amino acid sequence for a type of antibody fragment of the corresponding species.

Also provided is a F(ab')$_2$ fragment obtainable by expression of the fragment in a cell derived from a PER.C6™ cell.

Further provided is a crude preparation of an immunologically active antibody fragment obtainable by methods according to the invention. In certain embodiments, the immunologically active antibody fragment comprises a F(ab')$_2$ and a F(ab') fragment. Also provided is a F(ab')$_2$ fragment obtainable by separating a F(ab')$_2$ fragment from F(ab') fragments in the crude preparation. In one preferred embodiment, such F(ab')$_2$ fragments can selectively bind to activated vitronectin. Also provided is a F(ab')$_2$ fragment that can selectively bind to activated vitronectin.

Also provided is a pharmaceutical composition comprising an immunologically active antibody fragment according to the invention. Also provided is a pharmaceutical composition comprising a F(ab')$_2$ fragment according to the invention and a pharmaceutically acceptable carrier.

In another aspect, provided is a composition comprising immunologically active bivalent and monovalent antibody fragments in a ratio of at least 1:3, wherein the fragments are produced by a host cell according to the invention. In one preferred embodiment, the ratio is at least 3:1. Further provided is a composition comprising immunologically active bivalent and monovalent antibody fragments in a ratio of at least 1:3, wherein the fragments are obtainable by a method according to the invention.

Also provided is a vector useful in a method hereof, the vector comprising: a) DNA encoding VH1, CH1 and hinge region of an antibody, comprising introns, operably linked to a CMV promoter and a bovine growth hormone polyadenylation signal; b) DNA encoding VL and CL regions of an antibody, comprising an intron, operably linked to a CMV promoter and a bovine growth hormone polyadenylation signal, wherein the CMV promoter comprises nucleotides −735 to +95 from the CMV immediate early gene enhancer/promoter. In a preferred embodiment, the antibody binds to activated vitronectin. Also provided is a plasmid designated pcDNA3002(Neo) as deposited under number 01121318 at the ECACC on Dec. 13, 2001.

| A: | clone 243 | IgG |
| B: | clone 125 | IgG |
| C: | clone 195 | F(ab')$_2$ |
| D: | clone 118 | F(ab')$_2$. |

Figure 5:
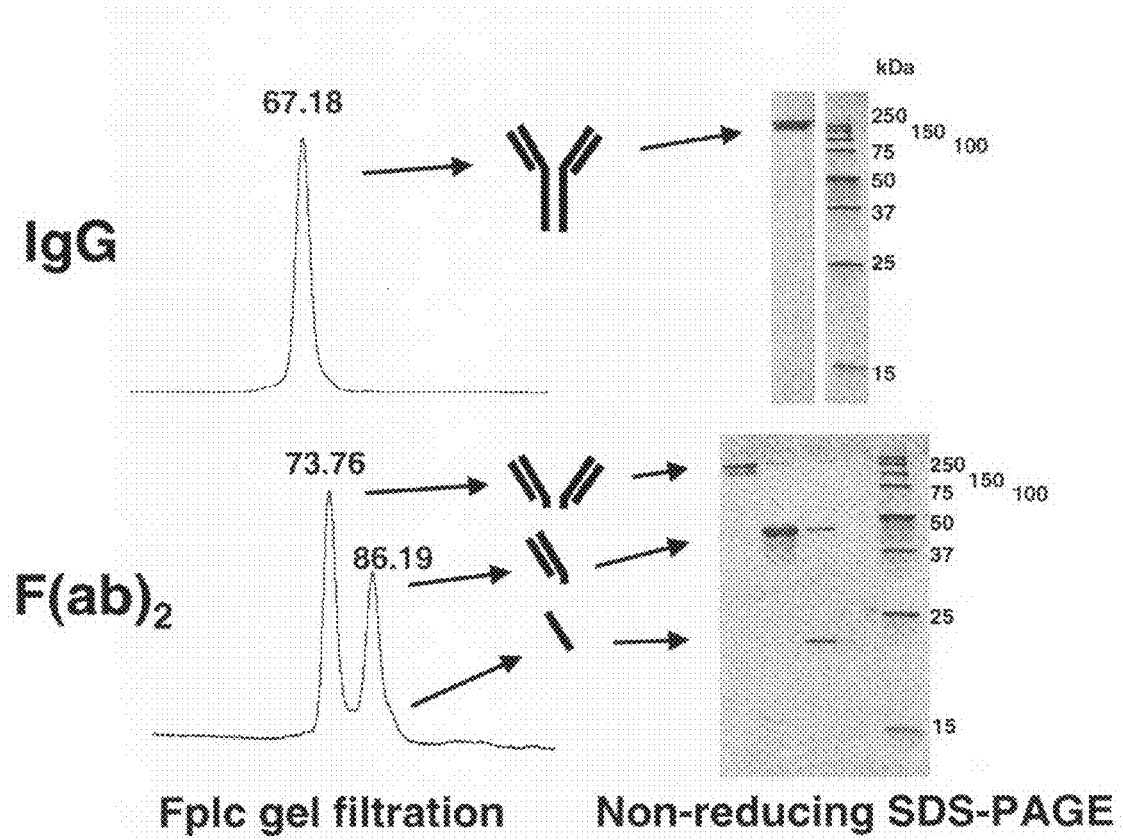

FIG. 5. Gel filtration analysis and non-reducing SDS-PAGE of purified samples of IgG and F(ab')$_2$ material. Elution times are indicated above peaks.

Figure 6:
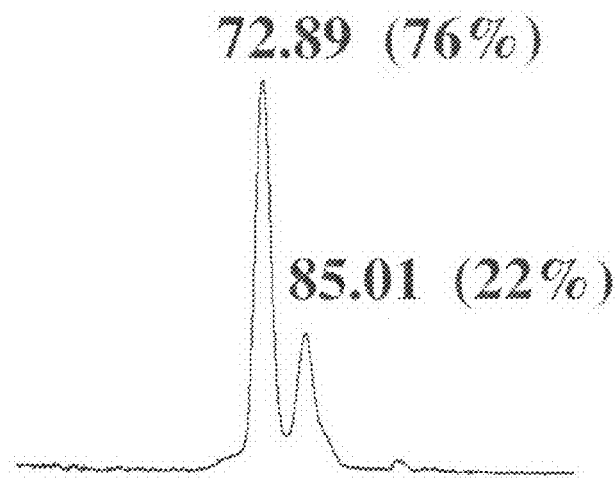

FIG. 6. Additional example of gel filtration of F(ab')$_2$ material. Elution volumes are indicated above peaks; F(ab')$_2$ (72.89 min.) accounts for 76% of material; F(ab') (85.01 min.) accounts for 22% of material.

Figure 7:
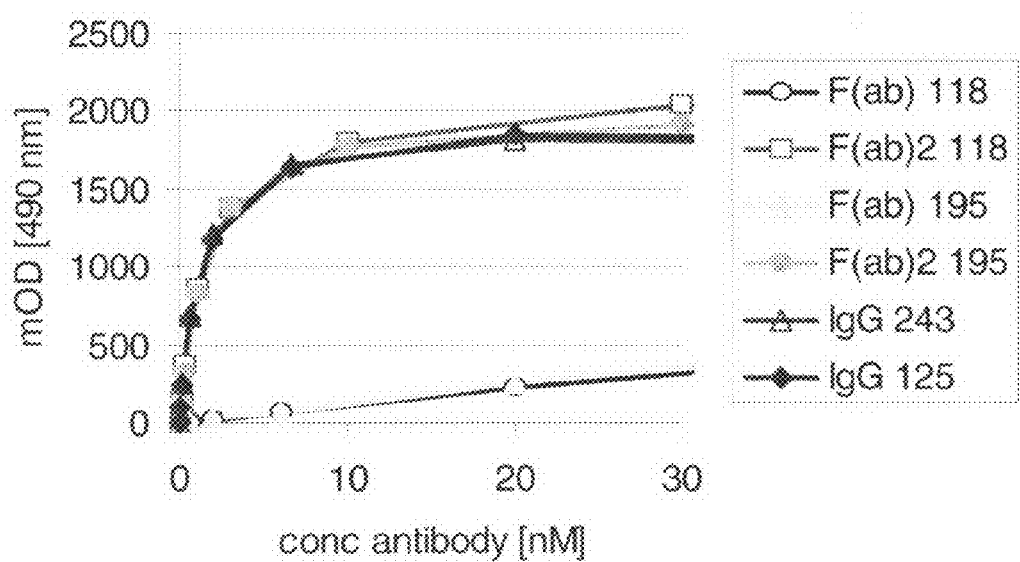

FIG. 7. Antigen binding of intact IgG (clones 243 and 125), F(ab')$_2$ and F(ab') (clones 118 and 195). F(ab') binds vitronectin approximately 100 times less efficiently than does IgG and F(ab')$_2$.

FIG. 8. Complete DNA sequence encoding the light chain of the anti-vitronectin IgG1 (this sequence is identical in both pVN18LcvHcv and pVN18LcvHcvHis).

FIG. 9. Complete DNA sequence encoding the complete heavy chain of the anti-vitronectin IgG1.

FIG. 10. Complete DNA sequence encoding the truncated (F(ab')$_2$) heavy chain fragment of anti-vitronectin IgG1, with His-tag sequence underlined.

DETAILED DESCRIPTION OF THE INVENTION

Provided is a host cell comprising adenovirus E1 sequences and further comprising recombinant nucleic acid encoding an immunologically active bivalent multimeric antibody fragment, and/or a precursor thereof, functionally linked to one or more sequences capable of driving expression of the fragment in the host cell. Methods of producing an immunologically active bivalent antibody fragment are also provided comprising culturing a host cell according to the invention.

Host Cell, Immortalized Primary Cell

Host cells for recombinant protein production are known in the art. In one aspect, the host cell hereof comprises adenovirus E1 sequences, preferably by comprising a nucleic acid sequence encoding at least one E1 protein of an adenovirus or a homologue, fragment and/or derivative thereof. These may be functional in immortalizing a primary cell when expressed in the cell. The E1 protein may comprise the E1A protein that functions in transforming and immortalizing the host cell. Furthermore, the E1B protein of adenovirus may be expressed, which can repress apoptosis of the host cell. In one aspect, therefore, the host cell of the invention comprises at least part of the E1 region of an adenovirus, comprising E1A and E1B sequences in expressible format.

Immortalized cells are known in the art and can, in principle, grow indefinitely in contrast to primary cells that will die after a limited number of cell divisions. Various tumor cell lines known in the art including, but not limited to, cell lines, such as Chinese hamster ovary (CHO), HeLa, or baby hamster kidney (BHK). Hybridoma cell lines including NS0 and Sp2-0 are also immortalized. A "primary cell," as meant herein, is a cell that is not derived from a tumor. To be able to grow indefinitely, a primary cell needs to be immortalized in some way. Immortalization of primary cells can, for instance, be achieved by introduction of the E1 region of an adenovirus in expressible form into the cells. Other possible methods include introduction of human papillomavirus (HPV) E6 and E7 sequences into the cells, introduction of SV40 T-antigen into the cells, mutation of endogenous p53 of the cells, transfection with c-myc and a mutant p53 gene in the cells. A preferred cell line for use as a host cell according to the present invention, PER.C6™, was obtained as described, e.g., in U.S. Pat. No. 5,994,128. As described in that patent, PER.C6™ cells have been deposited at the ECACC under No. 96022940. Briefly, human embryonic retinoblasts were immortalized by introduction of the E1 region comprising E1A and E1B of adenovirus, wherein the E1A gene is driven by the human PGK promoter.

Immunologically Active

"Immunologically active," as used herein, means capable of selectively binding to an antigen, wherein selective binding is defined as binding with an affinity (Kd) of at least $5 \times 10^4$ liters/mole, more preferably, $5 \times 10^5$, even more preferably, more than $5 \times 10^6$, still more preferably, $5 \times 10^7$, or more. Typically, monoclonal antibodies may have affinities which go up to $10^{10}$ liters per mole, or even higher.

Bivalent Multimeric Antibody Fragment

IgGs typically have two identical Fab regions, i.e., two regions that bind antigen, and are, therefore, said to be bivalent. An "antibody fragment," as used herein, is meant to define a molecule that retains the binding function but lacks the region that mediates the effector functions. Accordingly, antibody fragments according to the invention lack at least the C-terminal constant domain of the heavy chain. More preferably, antibody fragments according to the invention lack both the C-terminal constant domains of the heavy chain (C2 and C3). A "bivalent antibody fragment," as used herein, is a fragment that comprises two binding regions. Each binding region comprises a light chain and a heavy chain fragment, which binding region may exist as a dimer (i.e. the heavy chain fragment and the light chain are bound to form a dimer) or as a monomer (e.g., in a single chain format (scFv)). The bivalent antibody fragments as used herein are dimeric in the sense that the two binding regions making up the bivalent antibody fragment are linked to each other, although not via peptide bonds. The binding regions may dimerize in different ways, e.g., through one or more cysteine-dependent S-bridges (sulfur bridges), such as in the hinge regions directly attached to the C1 region of the two heavy chains. At least two independent antigen-binding sites may both bind the same or each may bind different antigens.

"Monovalent antibody fragments," as used herein, have only one antigen-binding site. One non-limiting example of a monovalent antibody fragment is a F(ab') fragment. The two binding regions may or may not be identical and may or may not be monospecific, meaning that both binding regions recognize the same epitope with the same affinity, whereas the former means it may recognize the same epitope with different affinity or different epitopes.

Figure 1:
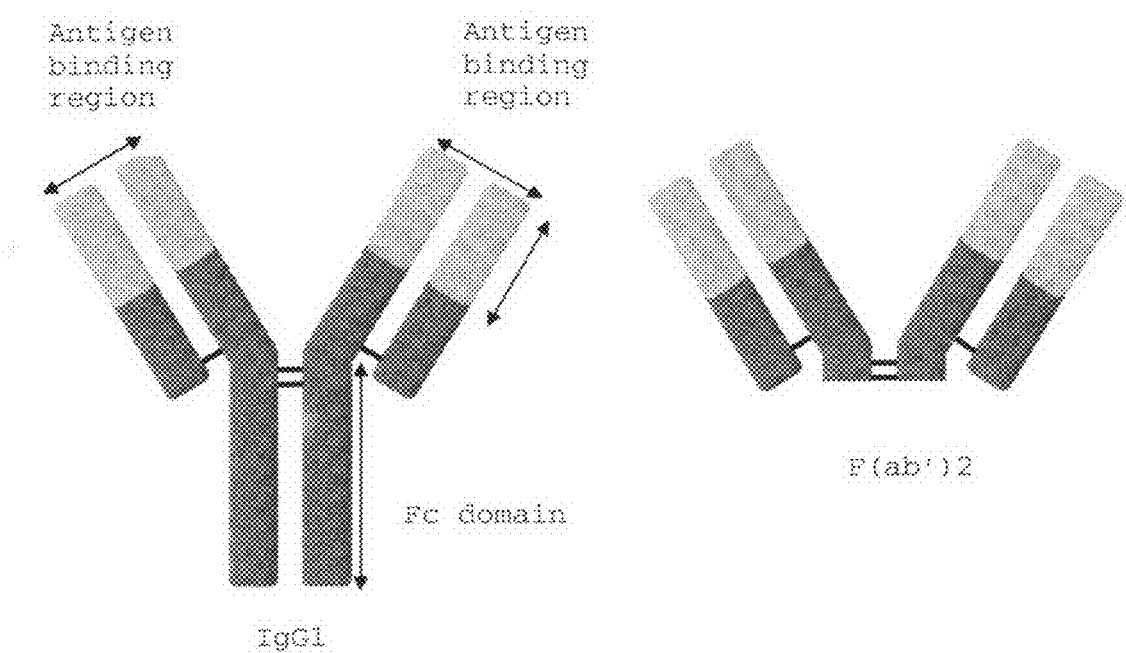
FIG. 1. Intact IgG (left) and F(ab')$_2$ fragment of IgG (right). Variable regions are pale, constant regions are dark. Disulphide bonds are marked in black.

A "preferred bivalent dimeric antibody fragment," as used herein, is a $F(ab')_2$ fragment that consists of two identical F(ab') fragments attached to each other through the heavy chain hinge regions by one or usually two sulfur bridges (FIG. 1).

A Conjugated Antibody Fragment

The antibody fragments produced may be labeled or conjugated with any moiety (radio- or fluorescent label, toxin, protein or other agents) in the same way as intact antibodies may be labeled. Labeling may also take the form of generation of a fusion protein in the cell line. Thus, antibody fragments may also be conjugated to other polypeptides, which conjugates or immunoconjugates are meant to be included in this invention. It is also possible to generate bispecific fragments, with antigen-binding sites situated either N-terminal or C-terminal to the hinge region.

Radiolabels may be used in both imaging and therapy. These may be alpha particle emitters such as Bismuth212 or Astatine211 that have a very high energy but only a small range, making bystander effects minimal. Beta particle emitters are more commonly in use; these include Iodine131, Yttrium90 and Rhenium186, amongst others. These have a lower particle energy, but a greater range, thus potentially causing bystander cell death in a tumor mass. In addition, antibodies may be labeled with cytotoxic moieties that kill the tumor cell upon internalization. An antibody linked to a bacterial toxin, calicheamicin, is currently on the market (Mylotarg; Carter, 2001). Other toxic moieties include maytansinoids (TAPs; ImmunoGen), as well as immunoliposomes loaded with chemotherapeutic agents, amongst others. Cargo may also be any number of proteins, peptides, drugs or prodrugs. It may also consist of a moiety to which a subsequently introduced therapeutic may bind.

There is also the potential to generate bispecific antibodies: one antigen-binding domain can bind a tumor cell, the other, a cell surface protein of an effector cell, thus inducing killing of the target cell. Homodimerization of fragments may also yield proteins with enhanced anti-tumor characteristics.

Antibody Fragment Precursor

Proteins can be encoded by precursor proteins that require peritranslational and/or posttranslational modifications before the mature protein form is reached. Nucleic acid-encoding precursor forms of antibody fragments, as well as the encoded precursor proteins themselves, including, but not limited to, pre-proteins containing secretion signals and the like, are included in the invention. The nucleic acid sequences encoding the fragments of interest may or may not comprise introns. Similarly, it may be a cDNA or cDNA-like nucleic acid, or a genomic fragment, or combinations thereof Sequences Capable of Driving Expression To obtain expression of nucleic acid sequences encoding antibody fragments or precursors thereof, it is well known to those skilled in the art that sequences capable of driving such expression have to be functionally (also called operably) linked to the nucleic acid sequences encoding the antibody fragments or precursors thereof. "Functionally linked" is meant to describe that the nucleic acid sequences encoding the antibody fragments or precursors thereof are linked to the sequences capable of driving expression such that these sequences can drive expression of the antibodies or precursors thereof. "Functionally linked" includes, but is not limited to, direct linkage. A non-limiting example of functional linkage is, for instance, found in expression cassettes. Sequences driving expression may include promoters, enhancers and the like, and combinations thereof. These should obviously be capable of functioning in the host cell, thereby driving expression of the nucleic acid sequences that are functionally linked to them. Promoters can be constitutive or regulated and can be obtained from various sources, including viruses, prokaryotic or eukaryotic sources, or artificially designed. These nucleic acid sequences are obtainable by standard techniques that are well known in the art. Expression of nucleic acids of interest may be from the natural promoter or derivative thereof or from an entirely heterologous promoter. Some well-known and much used promoters comprise promoters derived from viruses, such as adenovirus, such as the adenovirus E1A promoter, promoters derived from cytomegalovirus (CMV), such as the CMV immediate early (IE) promoter, or derived from eukaryotic cells, such as methallothionein (MT) promoters or elongation factor 1α (EF-1α) promoters. Any promoter or enhancer/promoter capable of driving expression of the sequence of interest in the host cell is thus suitable in the invention. In one preferred embodiment, the sequence capable of driving expression comprises a region from a CMV promoter, more preferably the region comprising nucleotides −735 to +95 of the CMV immediate early gene enhancer/promoter (CMVlong in FIG. 2). This region comprises a very strong enhancer (Boshart et al, 1985). It was found that this CMVlong works particularly well, resulting in several fold higher expression in comparison to the use of the shorter, regular CMV promoter as present in, e.g., the pcDNA3.1 plasmids (Invitrogen).

Culturing a cell is done to enable it to metabolize, grow and/or divide. This can be accomplished by methods well known to persons skilled in the art and includes, but is not limited to, providing nutrients for the cell. The methods comprise growth adhering to surfaces, growth in suspension, or combinations thereof. Several culturing conditions can be optimized by methods well known in the art to optimize protein production yields. Culturing can be done, for instance, in dishes, roller bottles or bioreactors, using batch, fed-batch, continuous systems, hollow fiber or other methods, all meant to be included in the invention. In order to achieve large-scale (continuous) production of recombinant proteins through cell culture, it is preferred in the art to have cells capable of growing in suspension and it is preferred to have cells capable of being cultured in the absence of animal- or human-derived serum or animal- or human-derived serum components. Thus, isolation is easier and safety is enhanced due to the absence of additional animal or human proteins derived from the culture medium, while the system is also very reliable as synthetic media are the best in reproducibility.

In certain embodiments, an immunologically active bivalent multimeric antibody fragment is a F(ab')$_2$ fragment. Expression of such fragments in eukaryotic cells has thus far been found to be problematic, as mostly F(ab') fragments were produced in the described systems. We provide here an immortalized primary eukaryotic host cell that is capable of expressing such F(ab')$_2$ fragments in a functional manner in significant amounts.

Host cells obtainable from mentioned cells are derived from the mentioned cells, for instance, by introducing nucleic acid sequences into the mentioned cells. This can be achieved by any method known in the art to introduce nucleic acid into cells, such as, transfection, lipofection, electroporation, virus infection, and the like. The method used for introducing nucleic acid sequences in cells is not critical for the current invention. Nucleic acid can be present in the cells extrachromosomally or stably integrated in the genome of the cells. Cells are capable of driving expression transiently, but preferably, the cells can drive expression in a stable manner. Alternatively, expression can be regulated.

In certain embodiments, the host cell provided is a mammalian cell, more preferably, a human cell, even more preferably, a human cell that is obtainable from the group consisting of 293 cells and PER.C6™ cells. PER.C6™ is a human cell line capable of expressing proteins in a highly reproducible, upscalable manner, as disclosed in WO 00/63403. Disclosed is that PER.C6™ cells are capable of producing immunologically active bivalent multimeric antibody fragments when a nucleic acid encoding such fragments functionally linked to sequences capable of driving expression of the fragments is present in the cells. Thus, in certain embodiments, the host cell is obtainable from a PER.C6™ cell.

The host cells hereof can be immortalized primary cells. Nucleic acid-encoding E1 protein of an adenovirus can immortalize cells and host cells according to the invention may be immortalized by the presence of the E1 nucleic acid sequence, such as is the case, for instance, in PER.C6™ cells. Other embryonic retinal cells, as well as amniocytes that have been immortalized by E1, can be useful in the present invention. Transformed human 293 cells (of embryonic kidney origin, cells also known as HEK293 cells) also have been immortalized by the E1 region from adenovirus (Graham et al., 1977), but PER.C6™ cells behave better in handling than the 293 cells. PER.C6™ cells have been characterized and documented extensively, while they behave significantly better in upscaling, suspension growth and growth factor independence. The fact that PER.C6™ cells can be brought in suspension in a highly reproducible manner, makes it very suitable for large-scale production.

Another aspect of the presence of a nucleic acid region of adenovirus E1, as compared to cells lacking this sequence, is that adenovirus E1A as a transcriptional activator is known to enhance transcription from certain promoters, including the CMV IE enhancer/promoter (Gorman et al., 1989; Olive et al., 1990). Thus, when the recombinant protein to be expressed is under the control of the CMV enhancer/promoter, as in one of the preferred embodiments of the invention, expression levels of the recombinant protein increase in cells comprising E1A. Host cells comprising a nucleic acid sequence encoding at least one E1 protein of an adenovirus or a homologue, fragment and/or derivative thereof functional may be used in immortalizing a primary eukaryotic cell.

The immunologically active bivalent multimeric antibody fragments can bind to any chosen antigen target. Methods to identify such targets and discover antibodies or antibody fragments to such targets are well known in the art. As an example, the present invention discloses production of F(ab')$_2$ fragments that selectively bind to activated vitronectin.

Preferably, antibodies or antibody fragments are of human origin but, of course, antibody fragments or antibodies can be of other origins as well.

An immunologically active bivalent antibody fragment, exemplified by a F(ab')$_2$ fragment, can be produced in several ways but, as discussed, a need exists for improved production methods of F(ab')$_2$ fragments. It would be particularly useful if eukaryotic host cells and methods for production of such fragment would be found that are characterized in improved ratios of produced F(ab')$_2$ fragments over F(ab') fragments, or generally improved ratios of immunologically active bivalent over monovalent antibody fragments. Thus, provided is a host cell expressing and secreting an immunologically active bivalent and monovalent antibody fragment and/or precursor thereof, wherein the ratio of secreted bivalent immunologically active antibody fragment to monovalent immunologically active antibody fragment by the host cell is at least 3:1, wherein the two antigen-binding regions of the bivalent active antibody fragment are not linked by peptide bonds. It will be understood by the skilled person that higher ratios are preferable. An example where this ratio is even higher than 3:1 is disclosed in the present invention.

It is possible to recombinantly produce bivalent multimeric antibody fragments and monovalent antibody fragments in a ratio of at least 1:3. Use of a hinge region that is derived from IgG3 in F(ab')$_2$ fragments has been reported to result in better ratios of F(ab')$_2$ to F(ab') fragments when compared to a hinge region derived from IgG1 (Leung et al., 1999). This is likely due to the high number of sulfur bridges (11 potential sulfur bridges) linking the two antibody-binding regions in an IgG3 hinge. However, increased numbers of sulfur bridges generally decrease production levels of the antibody fragments and it is, therefore, preferable to have fewer sulfur bridges for production on a large scale. This invention provides for a host cell and methods capable of expressing immunologically active bivalent and monovalent antibody fragments, of which the two antigen-binding regions are linked by only few sulfur bridges, in a much better ratio than achieved with the host cells and methods described till now.

Therefore, in certain embodiments, the two antigen-binding regions of the immunologically active bivalent and monovalent antibody fragments are linked by one to ten sulfur bridges, more preferably, by one or two sulfur bridges. The immunologically active bivalent fragments may be F(ab')$_2$ fragments.

Culturing the cells hereof can be done according to a variety of ways generally known and described in the art. Optimization of culturing conditions can be done to improve the yields of produced antibody fragments and to improve the ratio of secreted immunologically active bivalent multimeric to monovalent antibody fragments. Such optimization may include, but is not limited to, the growth media and additives, culturing temperature, time of growth and production phases, culture dish or bioreactor type and volume, and the like.

Growth media lacking animal- or human-derived serum or animal- or human-derived serum components may be used, such as, ExCell 525 (JRH) medium. Defined culture media are highly controllable and impose less safety issues and high reproducibility. They also are highly beneficial for downstream processing steps, when the desired proteins or protein fragments are to be isolated.

In certain embodiments, the immunologically active antibody fragments are isolated and/or purified. Any step that improves the ratio of the desired product to any byproducts can be used to achieve this and is meant to be included herein. Many methods are known in the art for isolating and/or purifying, and some non-limiting examples are filtration, centrifugation, chromatography, including, for instance, affinity-chromatography, hydrophobic interaction, size-fractionation, anion-exchange, cation-exchange, and the like. In the example, size-fractionation is performed to separate the F(ab')$_2$ from the F(ab') fragments.

Immunologically active bivalent antibody fragments, exemplified by F(ab')$_2$ fragments, can be produced by protease (e.g., pepsin) digestion of complete antibodies but, as discussed, this method has several disadvantages. Herein, a method is provided that is able to produce large quantities of functional bivalent antibody fragments without the use of protease steps.

It is another aspect to provide F(ab')$_2$ fragments obtainable by expression of the fragments in a cell derived from a PER.C6™ cell. Such F(ab')$_2$ fragments are efficiently obtainable in high amounts.

According to another aspect, a crude preparation of an immunologically active antibody fragment is provided, obtainable by methods according to the invention. A crude preparation may include the culture medium used to culture the cells and any preparation comprising the immunologically active antibody fragments somewhere in the process of purifying the desired material. In certain embodiments, the immunologically active antibody fragments comprise F(ab')$_2$ and F(ab') fragments. In another aspect, the F(ab')$_2$ fragments obtainable by separating the F(ab')$_2$ fragments from F(ab') fragments in the crude preparation are provided. Separation can be done according to any method known in the art including, but not limited to, size exclusion chromatography, affinity chromatography, anion- and/or cation-exchange, centrifugation, or filtration. Separation methods based on mass or size of the fragments are particularly useful for this purpose.

Also included herein are pharmaceutical compositions comprising an immunologically active antibody fragment, preferably a F(ab')$_2$ fragment hereof. Pharmaceutical compositions may or may not include carriers for administration of the desired material to humans or animals. Such carriers may include, but are not limited to, salts, sugars, proteins, or lipids. The administration of pharmaceutical compositions may be done in a variety of ways, which are not critical for the present invention. One non-limiting example for the use of pharmaceutical compositions according to the present invention comprises the administration of a F(ab')$_2$ fragment with a desired specificity in the form of a pharmaceutical composition to a human for imaging purposes, for instance, to locate a tumor that is selectively bound by the F(ab')$_2$ fragment. Administration of F(ab')$_2$ fragment producible according to the invention for therapeutic purposes is also possible.

Provided is a vector useful in a method hereof. The vector will comprise DNA encoding VH1, CH1 and hinge region of an antibody, optionally comprising introns. VH1 is the variable region of the heavy chain and CH1 is the first constant region of the heavy chain as present in a complete IgG. The hinge region is situated just behind the CH1 region and is generally the part where the two antigen-binding sites of an antibody are linked via cysteine-dependent sulfur bridges. The vector also will comprise DNA encoding the VL and CL regions of an antibody, optionally comprising an intron. VL and CL are the variable and constant regions of the light chain, respectively.

A vector is a DNA sequence capable of replicating in host cells and can, but need not, be a plasmid, phagemid, phage, yeast artificial chromosome, and the like. It usually comprises at least a sequence responsible for replicating the DNA in a host. The vector may also comprise selectable marker DNA, conferring to the host cell in which the vector is present the ability to grow in the presence of a toxic substrate or in the absence of an otherwise essential growth factor. The vector may comprise replication signals for propagation in a microbial host so it can easily be obtained in quantities that are practical. The region comprising DNA encoding VH, CH1 and hinge region (heavy chain fragment) may be of genomic origin or may be cDNA in which artificial introns are optionally present. The same holds for the region comprising DNA encoding VL and CL (light chain fragment). DNA of the VH, CH and hinge, as well as for VL and CL, should be in such a constellation that both a heavy and a light chain transcription product is formed, which upon splicing, can be translated into functional protein comprising a heavy and a light chain fragment, respectively. DNA encoding precursors of the fragments is meant to be included in the invention. The heavy and light chain fragment-encoding DNA regions preferably encode human antibody fragments. Other protein-encoding DNA such that an immunofusion protein is encoded, may or may not be present. DNA encoding the heavy chain fragment and DNA encoding the light chain fragment can each be operably linked to a CMV promoter, such that the CMV promoter is capable of driving transcription of the DNA in a suitable cell described in the invention. The CMV promoter is a strong promoter useful for driving expression of recombinant proteins to high levels, for instance, as described in U.S. Pat. No. 5,168,062. The CMV promoter as used herein comprises nucleotides −735 to ++95 of the major immediate early gene enhancer/promoter, wherein the nucleotides are numbered relative to the transcriptional start site. This region comprises the enhancer and promoter of the CMV immediate early promoter and the person skilled in the art may make substitutions, insertions and/or deletions in this region, test the promoter for usefulness according to methods known in the art, and use such a mutated CMV enhancer/promoter according to the invention without departing herefrom. The use of this promoter further has the advantage that E1 sequences as present in host cells according to the invention can augment transcription rates from this promoter. Furthermore, both DNA encoding the heavy chain fragment and the light chain fragment can be operably linked to a polyadenylation signal, preferably from the bovine growth hormone gene. Such a signal is useful for conferring good polyadenylation of the transcripts, resulting in better translation and, hence, in higher recombinant product yields (e.g., as disclosed in U.S. Pat. No. 5,122,458). As disclosed herein, an example has been reduced to practice where the antibody fragments encoded by the vector can form F(ab')$_2$ fragments that selectively bind to activated vitronectin. The VH and VL regions of the vector can encode any VH and VL region, which determine the antigen specificity of the resulting antibody fragments.

Methods to obtain DNA sequences encoding VH and VL comprising regions of interest are known to those in the art. These include, but are not limited to, obtaining such DNA from hybridoma cells or, for instance, by phage display. The fragments can then be cloned by standard techniques, either directly or via extra steps into the vector of the invention. The vector provided in the invention is particularly useful for use in the host cells of the invention, as it was found that it can give rise to high expression levels of the desired proteins.

Figure 2:
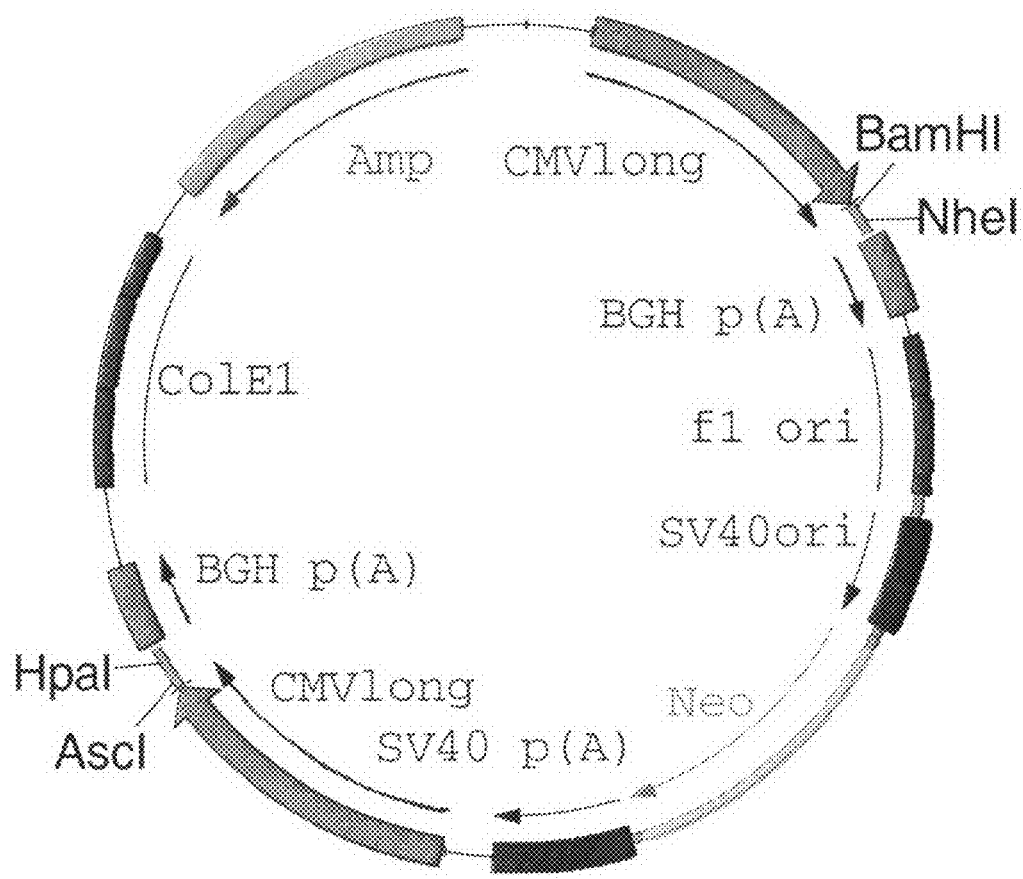
FIG. 2. Expression vectors.

Also provided is a plasmid useful for expression of recombinant proteins in host cells in general, plasmid pcDNA3002 (Neo) FIG. 2, deposited on Dec. 13, 2001, at the European Collection of Cell Cultures (ECACC) under number 01121318. This plasmid has been found to be particularly useful for expression of multiple proteins and dimeric proteins, including immunoglobulins and fragments thereof, in the host cells of the invention. The DNA encoding the protein(s) or fragments of interest can be cloned behind the CMVlong promoters in this plasmid by standard techniques well known to persons skilled in the art.

The following illustrative Examples are provided, which are not intended to limit the scope of the invention. DNA encoding a complete antibody, as well as the antibody fragments constituting a F(ab')$_2$ fragment directed against activated vitronectin, were cloned and expressed in PER.C6™ cells. Expression was shown and, after purification, the vitronectin-binding activity of the resulting proteins was demonstrated.

EXAMPLE 1

Construction of Expression Vectors

Figure 3:
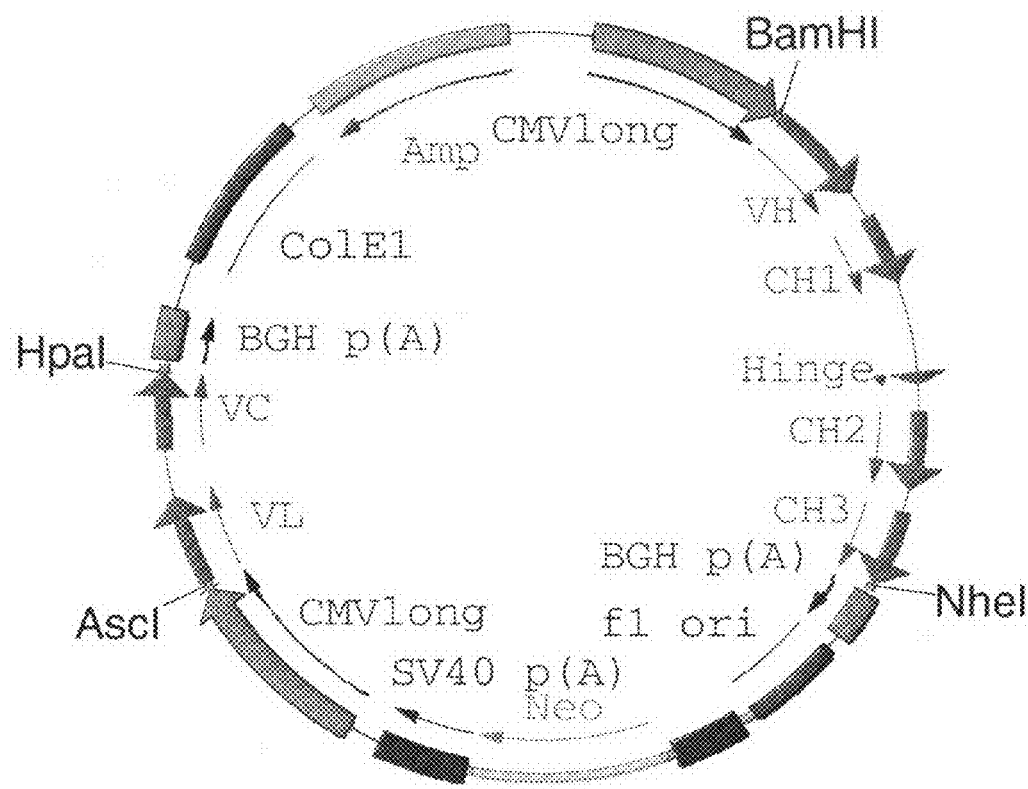
FIG. 3. Vectors for expression of intact IgG or F(ab')$_2$ fragment of IgG.

An expression plasmid was generated that encodes both the light and heavy chains of an IgG1 antibody that recognizes activated vitronectin (as disclosed in EP 1130099). The DNA encoding the antigen-binding region of this antibody was first isolated from a scFv phage display library and a leader sequence and constant regions were added prior to cloning into the expression vector pcDNA3002(Neo) (FIG. 2). The expression vector pcDNA3002(Neo) was deposited on Dec. 13, 2001, at the European Collection of Cell Cultures (ECACC) under number 01121318. The resulting plasmid is pVN18LcvHcv (FIG. 3), which was deposited on Dec. 13, 2001, at the ECACC under number 01121320. In addition, a plasmid was constructed that contains an intact light chain and a heavy chain truncated immediately after the last translated codon of the hinge region. This was followed by a sequence encoding a 6 Histidine tag and then a stop codon. This plasmid, pVN18LcvHcvHis, can express a F(ab')$_2$ fragment (FIG. 3) and was deposited on Dec. 13, 2001, at the ECACC under number 01121319. An additional plasmid has also been generated for F(ab')$_2$ production that does not contain a sequence encoding a His-tag. Procedures were performed essentially as described in Sambrook and Russell, 2001.

Generation of pVN18LcvHcv and pVN18LcvHcvHis

Variable regions of the light and heavy chains of the anti-vitronectin antibody were isolated from a phage display library. These were separately cloned into vectors while also adding leader (signal) sequences at the N-termini and constant regions at the C-termini of the two chains, resulting in plasmids VL VN18 and VH VN18 comprising the light and heavy chains, respectively. The light chain of the anti-vitronectin IgG is a kappa type of chain. This will be present in both expression plasmids and so was inserted first into pcDNA3002 (Neo). Plasmid VL VN18 was used as a template for PCR of the kappa light chain and to include convenient restriction sites (for general molecular cloning procedures, see, e.g., Sambrook and Russel, 2001).

```
Oligo E001:                                    (SEQ ID NO:1)
CCTGGCGCGCCACCATGGCATGCCCTGGCTTCCTGTGG.
```

This is homologous to the start of the translated sequence. The start codon is in bold; the Kozak sequence is underlined; the AscI site used for cloning is in italics.

```
                                               (SEQ ID NO:2)
Oligo E002:    CCGGGTTAACTAACACTCTCCCCTGTTGAAGC.
```

This is homologous to the non-coding strand at the end of the translated sequence. The stop codon is in bold; the HpaI site used for cloning is in italics.

Using these oligonucleotides, the light chain was amplified using Pwo polymerase as a 1.3 kb fragment, digested with AscI and HpaI and ligated into pcDNA3002(Neo) digested with the same enzymes. The resulting plasmid is pVN18Lcv (not shown).

Two forms of the heavy chain were then inserted into this plasmid to generate either the intact IgGI molecule or the F(ab')$_2$ fragment. Plasmid VH VN18 was used as a template for PCR amplification.

For production of the intact IgG1, the following oligonucleotides were used:

(SEQ ID NO:3)
E003:   GGA*GGATCC*GCCACCATGGCATGCCCTGGCTTCCTGTGG.

This is homologous to the start of the translated sequence. The start codon is in bold; the Kozak sequence is underlined; the BamHI site used for cloning is in italics.

(SEQ ID NO:4)
E004:   GGAT*GGCTAGC*TCATTTACCCGGAGACAGGGAGAG.

This is homologous to the non-coding strand at the end of the translated sequence. The stop codon is in bold; the NheI site used for cloning is in italics.

Using these oligonucleotides, the heavy chain was amplified using Pwo polymerase as a 2.2 kb fragment, digested with BamHI and NheI and ligated into pVN18Lcv digested with the same enzymes. The resulting plasmid is pVN18LcvHcv.

For generation of the His-tagged F(ab')$_2$ fragment, the following oligonucleotides were used to PCR the heavy chain fragment from VH VN18:

(SEQ ID NO:3)
E003:   GGA*GGATCC*GCCACCATGGCATGCCCTGGCTTCCTGTGG.

This is homologous to the start of the translated sequence. The start codon is in bold; the Kozak sequence is underlined; the BamHI site used for cloning is in italics.

E005:   (SEQ ID NO:5)
GGAT*GGCTAGC*TCAATGGTGATGGTGATGATGTGGGCACGGTGGGCATGT

GTGAGTT.

This is homologous to the non-coding strand at the end of the translated sequence. The stop codon is in bold; the NheI site used for cloning is in italics and the sequence coding for six histidine residues forming the His-tag is underlined. Thus, the amino acid sequence at the terminus of the heavy chain is:
Glu Pro Lys Ser Cys Asp Lys Thr His Thr Cys Pro Pro Cys Pro His His His His His His Stop (SEQ ID NO:6).

Using these oligonucleotides, the heavy chain fragment was amplified from plasmid VH VN18 as a 1.3 kb fragment using Pwo polymerase, digested with BamHI and NheI and ligated into pVN18Lcv digested with the same enzymes. The resulting plasmid is pVN18LcvHcvHis.

The sequences of the antibody-encoding regions are shown in FIGS. 8-10.

EXAMPLE 2

Transfection of PER.C6™ Cell Lines and Production of F(ab')$_2$ Fragments

Cells were transfected with either pVN18LcvHcv or pVN18LcvHcvHis by a lipofectamine-based method. In brief, PER.C6™ cells were seeded at $3.5 \times 10^6$ cells per 96 mm tissue culture dish. For each dish, 2 μg plasmid DNA was mixed with 10 μl lipofectamine (Gibco); this was added to the cells in serum-free DMEM medium (total volume 7 ml) and incubated for 5 hours. This was then replaced with complete medium. The following day (and for the ensuing 3 weeks), cells were grown in DMEM in the presence of 0.5 mg/ml Geneticin (G418) to select for clones that were stably transfected with the plasmid. Clones secreting high levels of monoclonal into the cell culture supernatant were selected by an ELISA assay. In brief, wells of a 96-well plate were coated with antibody raised against Ig kappa light chain. After blocking with a milk solution, samples were added to wells at varying dilutions and incubated for 1 hour. After washing, detection antibody (biotin-labeled anti-IgG) was applied for 30 minutes. After a further washing step, this was detected by addition of streptavidin-horse radish peroxidase, followed by a final wash and addition of substrate O-phenylene diamine dihydrochloride. Antibody concentration was determined by comparing optical density at 492 nm with that of a known antibody standard.

The top producing clones from each transfection (IgG or F(ab')$_2$) were selected for further analysis. These were:

| Intact IgG: | clones 125 and 243 |
| --- | --- |
| F(ab')$_2$: | clones 118 and 195 |

Figure 4:
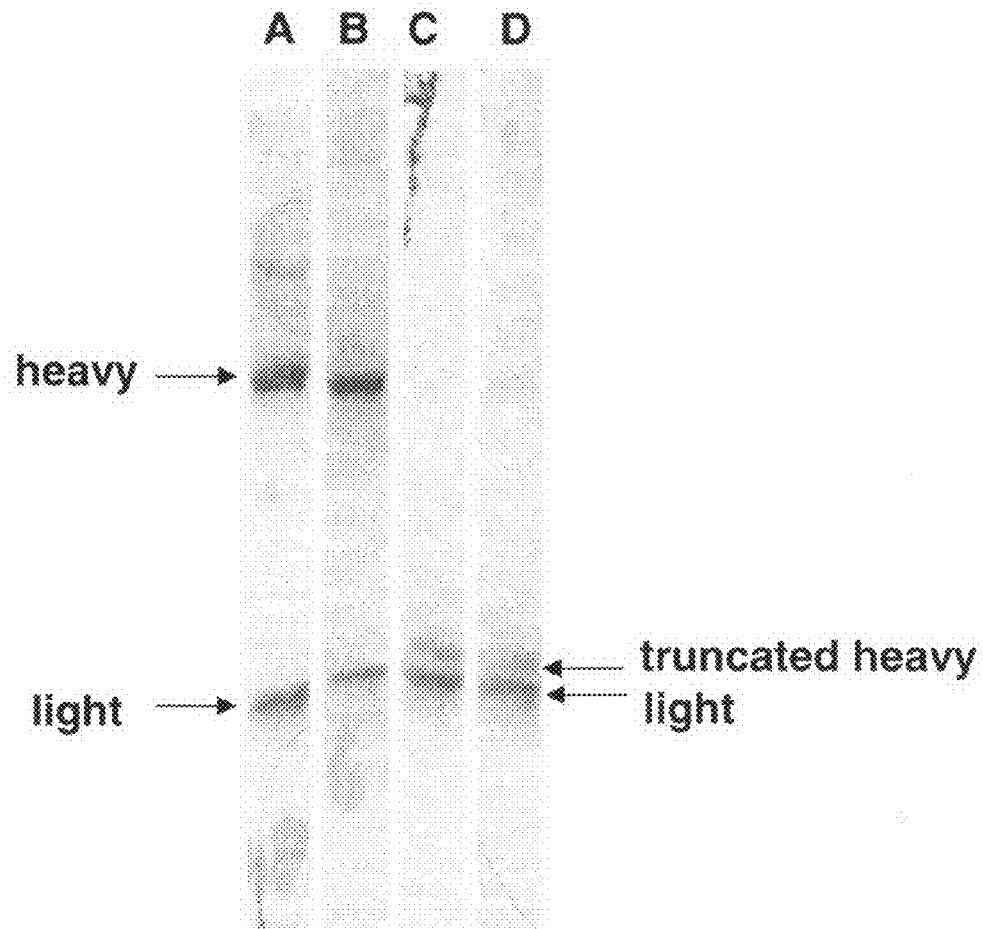
FIG. 4. Reducing SDS-PAGE of cell culture supernatant from clones producing intact IgG and F(ab')$_2$ fragments.

Production of antibody is performed in serum-free medium. Thus, the adherent cells in tissue culture flasks were washed with PBS, then EXCELL 525™ medium (JRH Biosciences) was added and the cells incubated further for 4 days to allow secreted antibody to accumulate in the cell culture medium. A sample of the medium was electrophoresed on reducing SDS-PAGE (FIG. 4). The heavy and light chains that comprise the intact, secreted antibody are the predominant protein species. The truncated heavy chain of the F(ab')$_2$ fragment is present at a lower concentration than either the light chain or the intact heavy chain of IgG. The material was then purified: intact IgG was purified over a Protein A column and F(ab')$_2$ fragments over a Protein L column (Protein L binds kappa light chains). Purified material was dialyzed into PBS and then analyzed by gel filtration on a HILOAD 16/60 SUPERDEX™ 200 column. The results of the gel filtration for clone 243 (intact IgG) and 118 (F(ab')$_2$) are shown in FIG. 5. The results are identical to those seen for clone 125 (IgG) and clone 195 (F(ab')$_2$) for which data is not shown. Intact IgG runs as a single peak with elution time 67.18 (as expected for a protein of 150 kDa). The F(ab')$_2$ fragment runs as two main peaks; elution times suggest that the first is F(ab')$_2$ and the second is F(ab'). This was confirmed by electrophoresis over non-reducing SDS-PAGE (FIG. 5).

Subsequent purifications indicated that the ratio of F(ab')$_2$:F(ab') is often better. This is shown in FIG. 6, again for clone 118, where the percentage of F(ab')$_2$ and F(ab') are 76% and 22%, respectively. Similar results were also obtained with the constructs lacking a His-tag.

The efficiency of binding to antigen was determined for intact IgG, F(ab')₂ and F(ab'). The antibody described above was raised against activated vitronectin, thus, vitronectin was purified in this form (Yatohgo et al., 1988) and bound to the wells of a 96-well plate. Upon an ELISA analysis, the IgG and F(ab')₂ material from two different clones bound equally efficiently, whereas the F(ab') material bound the vitronectin approximately 100-fold less efficiently FIG. 7). This indicates that the F(ab')₂ produced by this method does indeed bind antigen with equal avidity as the intact divalent IgG.

REFERENCES

Behr T., Becker W., Hannappel E., Goldenberg D. M., Wolf F. (1995). Targeting of liver metastases of colorectal cancer with IgG, F(ab')₂, and F(ab') anti-carcinoembryonic antigen antibodies labeled with 99mTc: the role of metabolism and kinetics. Cancer Res. 55 (23 Suppl.), 5777s-5785s.

Borrebaeck C. A. K. and Carlsson R. (2001). Human therapeutic antibodies. Curr. Op. Pharmacol. 1, 404-408.

Boshart W., Weber F., Jahn G., Dorsch-Hasler K., Fleckenstein B., Schaffner W. (1985). A very strong enhancer is located upstream of an immediate early gene of human cytomegalovirus. Cell 41, 521-530.

Carter P. (2001). Improving the efficacy of antibody-based cancer therapies. Nature Reviews: Cancer 1, 118-129.

De Sutter K., Feys V., Van de Voorde A., Fiers W. (1992). Production of functionally active murine and murine::human chimeric F(ab')₂ fragments in COS-1 cells. Gene 113, 223-30.

George A. J. T. and Urch C. E. (2000). Diagnostic and therapeutic antibodies. Pub. Humana Press.

Gorman C. M., Gies D., McCray G., Huang M. (1989). The human cytomegalovirus major immediate early promoter can be transactivated by adenovirus early proteins. Virology 171, 377-385.

Graham F. L., Smiley J., Russell W. C., Nairn R. (1977). Characteristics of a human cell line transformed by DNA from adenovirus type 5. J. Gen. Virol. 36, 59-72.

Humphreys D. P., Vetterlein O. M., Chapman A, P., King D. J., Antoniw P., Suitters A. J., Reeks D. G., Parton T. A. H., King L. M., Smith B. J., Lang V. and Stephens P. E. (1998). F(ab')₂ molecules made from *Escherichia coli* produced F(ab') with hinge sequences conferring increased serum survival in an animal model. J. Imm. Methods 217, 1-10.

King D. J., Adair J. R., Angal S., Low D. C., Proudfoot K. A., Lloyd J. C., Bodmer M. W., Yarranton G. T. (1992). Expression, purification and characterization of a mouse-human chimeric antibody and chimeric F(ab') fragment. Biochem. J. 281, 317-23.

King D. J., Turner A., Farnsworth A. P., Adair J. R., Owens R. J., Pedley R. B., Baldock D., Proudfoot K. A., Lawson A. D., Beeley N. R., et al. (1994). Improved tumor targeting with chemically cross-linked recombinant antibody fragments. Cancer Res. 154, 6176-85.

Leung S., Qu Z., Hansen H., Shih L., Wang J., Losman M., Goldenberg D., Sharkey R. (1999). The effects of domain deletion, glycosylation, and long IgG3 hinge on the biodistribution and serum stability properties of a humanized IgG1 immunoglobulin, hLL2, and its fragments. Clinical Cancer Research vol. 5, 3106s-3117s.

Olive D. M., Al-Mulla W., Simsek M., Zarban S., al-Nakib W. (1990). The human cytomegalovirus immediate early enhancer-promoter is responsive to activation by the adenovirus-5 13S E1A gene. Arch. Virol. 112, 67-80.

Park J. W. and Smolen J. (2001). Monoclonal antibody therapy. Adv. Prot. Chem. 56, 369-421.

Sambrook J. and Russell D. W. (2001). Molecular cloning: a laboratory manual. Pub. Cold Spring Harbor Laboratory Press.

Tutt A. L., French R. R., Illidge T. M., Honeychurch J., McBride H. M., Penfold C. A., Fearon D. T., Parkhouse R. M. E., Klaus G. G. B. and Glennie M. J. (1998). Monoclonal antibody therapy of B cell lymphoma: signaling activity on tumor cells appears more important than recruitment of effectors. J. Immunol. 161, 3176-3185.

Willuda J., Kubetzko S., Waibel R., Schubiger P. A., Zangemeister-Wittke U., Pluckthun A. (2001). Tumor targeting of mono-, di-, and tetravalent anti-p185(HER-2) miniantibodies multimerized by self-associating peptides. J. Biol. Chem. 276, 14385-92.

Yokota T., Milenic D. E., Whitlow M., Schlom J. (1992). Rapid tumor penetration of a single-chain Fv and comparison with other immunoglobulin forms. Cancer Res. 52, 3402-3408.

Zapata G., Ridgway J. B., Mordenti J., Osaka G., Wong W. L., Bennett G. L., Carter P. (1995). Engineering linear F(ab')₂ fragments for efficient production in *Escherichia coli* and enhanced antiproliferative activity. Protein Eng. 8, 1057-62.

What is claimed is:

1. A process for producing a F(ab')$_2$ fragment in a ratio of at least 1:1 with a corresponding F(ab') fragment by the recombiant expression from a cell, process comprising the steps of:

provding a cell deposited at the European Collection of Cell Cultures ("ECACC") under number 96022940, said cell further comprising:

one or more nucleic acids comprising sequences capable of driving expression operably linked to nucleotide sequences encoding F(ab')$_2$ fragments;

culturing the cell in a suitable medium; and expressing the one or more nucleic acids to produce from the cell the F(ab')$_2$ fragment, wherein the F(ab')$_2$ fragment and the corresponding F(ab') fragment are secreted from the cell in a ratio of at least 1:1.

2. The process of claim 1, further comprising purifying the F(ab')$_2$ fragment.

3. The process of claim 1, wherein the F(ab')$_2$ fragment and the F(ab') fragment are secreted from the cell in a ratio of at least 2:1.

4. The process of claim 1, wherein the F(ab')$_2$ fragment and the F(ab') fragment are secreted from the cell in a ratio of at least 3:1.

5. The process of claim 1, wherein the sequences capable of driving expression comprise a nucleic acid sequence from a cytomegalovirus (CMV) immediate early gene enhancer/promoter.

6. The process of claim 1, wherein the nucleotide sequences encoding the F(ab')$_2$ fragments comprise at least one intron.

7. The process of claim 1, wherein the F(ab')$_2$ fragments' antigen binding regions are linked by at least one, but not more than 10 disulfide bonds.

8. The process of claim 7, wherein the antigen binding regions are linked by one or two disulfide bonds.

9. A method for improving a ratio of expressed F(ab')$_2$ fragments to F(ab') fragments by recombinant expression from cells as compared to expression from Chinese Hamster Ovary (CHO) cells, the process comprising:

providing a cell deposited at the European Collection of Cell Cultures ("ECACC") under number 96022940 having one or more recombinant nucleic acids comprising sequences capable of driving expression operably linked to nucleotide sequences encoding F(ab')$_2$ fragments;

culturing the cell in a suitable medium; and expressing the one or more nucleic acids to produce from the cell the F(ab')$_2$ fragment, so as to improve the ratio of expression F(ab')$_2$ fragments to F(ab') fragments to a ratio of at least 1:1.

* * * * *

UNITED STATES PATENT AND TRADEMARK OFFICE
CERTIFICATE OF CORRECTION

| | | |
|---|---|---|
| PATENT NO. | : 7,537,916 B2 | |
| APPLICATION NO. | : 12/070145 | |
| DATED | : May 26, 2009 | |
| INVENTOR(S) | : David Halford Ashton Jones and Abraham Bout | |

It is certified that error appears in the above-identified patent and that said Letters Patent is hereby corrected as shown below:

COLUMN 13, LINE 23,    change "-735 to ++95" to --735 to +95--

CLAIM 1,    COLUMN 25, LINE 4,    change "a cell, process" to --a cell, the process--

Signed and Sealed this
Eighth Day of March, 2011

David J. Kappos
*Director of the United States Patent and Trademark Office*

SEQUENCE LISTING

```
<160> NUMBER OF SEQ ID NOS: 9

<210> SEQ ID NO 1
<211> LENGTH: 38
<212> TYPE: DNA
<213> ORGANISM: Artificial Sequence
<220> FEATURE:
<223> OTHER INFORMATION: Oligo E001

<400> SEQUENCE: 1
cctggcgcgc caccatggca tgccctggct tcctgtgg                            38

<210> SEQ ID NO 2
<211> LENGTH: 32
<212> TYPE: DNA
<213> ORGANISM: Artificial Sequence
<220> FEATURE:
<223> OTHER INFORMATION: Oligo E002
```

```
<400> SEQUENCE: 2
ccgggttaac taacactctc ccctgttgaa gc                                  32

<210> SEQ ID NO 3
<211> LENGTH: 39
<212> TYPE: DNA
<213> ORGANISM: Artificial Sequence
<220> FEATURE:
<223> OTHER INFORMATION: Oligo E003

<400> SEQUENCE: 3
ggaggatccg ccaccatggc atgccctggc ttcctgtgg                           39

<210> SEQ ID NO 4
<211> LENGTH: 35
<212> TYPE: DNA
<213> ORGANISM: Artificial Sequence
<220> FEATURE:
<223> OTHER INFORMATION: Oligo E004

<400> SEQUENCE: 4
ggatggctag ctcatttacc cggagacagg gagag                              35

<210> SEQ ID NO 5
<211> LENGTH: 57
<212> TYPE: DNA
<213> ORGANISM: Artificial Sequence
<220> FEATURE:
<223> OTHER INFORMATION: Oligo E005

<400> SEQUENCE: 5
ggatggctag ctcaatggtg atggtgatga tgtgggcacg gtgggcatgt gtgagtt      57

<210> SEQ ID NO 6
<211> LENGTH: 21
<212> TYPE: PRT
<213> ORGANISM: Artificial Sequence
<220> FEATURE:
<223> OTHER INFORMATION: amino acid sequence at the terminus of the
      heavy chain

<400> SEQUENCE: 6

Glu Pro Lys Ser Cys Asp Lys Thr His Thr Cys Pro Pro Cys Pro His
1               5                   10                  15

His His His His His
            20

<210> SEQ ID NO 7
<211> LENGTH: 910
<212> TYPE: DNA
<213> ORGANISM: Artificial Sequence
<220> FEATURE:
<223> OTHER INFORMATION: Light chain of anti-vitronectin IgG1

<400> SEQUENCE: 7
atggcatgcc ctggcttcct gtgggcactt gtgatctcca cctgtcttga attttccatg   60
gctgaaattg agctcaccca gtctccatcc tccctgtctg catctgtagg agacagagtc  120
accatcactt gccgggcaag tcagagcatt agcagctatt taaattggta tcagcagaaa  180
ccagggaaag cccctaagct cctgatctat gctgcatcca gtttacaaag tggggtccca  240
tcaaggttca gtggcagtgg atctgggaca gatttcactc tcaccatcag cagtctgcaa  300
cctgaagatt ttgcaactta ctactgtcag cagaggaggg ctatgcctac gaagttcggc  360
```

-continued

| | |
|---|---|
| ggagggacca aggtggagat caaacgtaag tgcactttgc ggccgctagg aagaaactca | 420 |
| aaacatcaag attttaaata cgcttcttgg tctccttgct ataattatct gggataagca | 480 |
| tgctgttttc tgtctgtccc taacatgccc tgtgattatc cgcaaacaac acacccaagg | 540 |
| gcagaacttt gttacttaaa caccatcctg tttgcttctt tcctcaggaa ctgtggctgc | 600 |
| accatctgtc ttcatcttcc cgccatctga tgagcagttg aaatctggaa ctgcctctgt | 660 |
| tgtgtgcctg ctgaataact tctatcccag agaggccaaa gtacagtgga aggtggataa | 720 |
| cgccctccaa tcgggtaact cccaggagag tgtcacagag caggacagca aggacagcac | 780 |
| ctacagcctc agcagcaccc tgacgctgag caaagcagac tacgagaaac acaaagtcta | 840 |
| cgcctgcgaa gtcacccatc agggcctgag ctcgcccgtc acaaagagct tcaacagggg | 900 |
| agagtgttag | 910 |

<210> SEQ ID NO 8
<211> LENGTH: 2143
<212> TYPE: DNA
<213> ORGANISM: Artificial Sequence
<220> FEATURE:
<223> OTHER INFORMATION: Complete heavy chain of anti-vitronectin IgG1

<400> SEQUENCE: 8

| | |
|---|---|
| atggcatgcc ctggcttcct gtgggcactt gtgatctcca cctgtcttga attttccatg | 60 |
| gccgaggtgc agctggtgga gtctggggga ggcttggtac agcctggggg gtccctgaga | 120 |
| ctctcctgtg cagcctctgg attcaccttt agcagctatg ccatgagctg ggtccgccag | 180 |
| gctccaggga aggggctgga gtgggtctca gctattagtg gcagtggtgg tagcacatac | 240 |
| tacgcagact ccgtgaaggg ccggttcacc atctccagag acaattccaa gaacacgctg | 300 |
| tatctgcaaa tgaacagcct gagggccgag gacacggccg tgtattactg tgcaagagac | 360 |
| gaccggccta gggagttgga ctcctgggggc caaggtaccc tggtcaccgt ctcgacaggt | 420 |
| gagtgcggcc gcgagcccag acactggacg ctgaacctcg cggacagtta agaacccagg | 480 |
| ggcctctgcg ccctgggccc agctctgtcc cacaccgcgg tcacatggca ccacctctct | 540 |
| tgcagcctcc accaagggcc catcggtctt ccccctggca cctcctcca agagcacctc | 600 |
| tgggggcaca gcggccctgg gctgcctggt caaggactac ttccccgaac cggtgacggt | 660 |
| gtcgtggaac tcaggcgccc tgaccagcgg cgtgcacacc ttcccggctg tcctacagtc | 720 |
| ctcaggactc tactccctca gcagcgtggt gaccgtgccc tccagcagct gggcacccca | 780 |
| gacctacatc tgcaacgtga atcacaagcc cagcaacacc aaggtggaca gagagttgg | 840 |
| tgagaggcca gcacagggag ggagggtgtc tgctggaagc caggctcagc gctcctgcct | 900 |
| ggacgcatcc cggctatgca gtcccagtcc agggcagcaa gcaggcccc gtctgcctct | 960 |
| tcacccggag gcctctgccc gccccactca tgctcaggga gagggtcttc tggctttttc | 1020 |
| cccaggctct gggcaggcac aggctaggtg cccctaaccc caggccctgca cacaaagggg | 1080 |
| caggtgctgg gctcagacct gccaagagcc atatccggga ggaccctgcc cctgacctaa | 1140 |
| gcccacccca aaggccaaac tctccactcc ctcagtcgg acaccttctc tcctcccaga | 1200 |
| ttccagtaac tcccaatctt ctctctgcag agcccaaatc ttgtgacaaa actcacacat | 1260 |
| gcccaccgtg cccaggtaag ccagcccagg cctcgccctc cagctcaagg cgggacaggt | 1320 |
| gccctagagt agcctgcatc cagggacagg cccagccgg tgctgacac gtccacctcc | 1380 |
| atctcttcct cagcacctga actcctgggg ggaccgtcag tcttcctctt ccccccaaaa | 1440 |
| cccaaggaca cccctcatgat ctcccggacc cctgaggtca catgcgtggt ggtggacgtg | 1500 |

-continued

```
agccacgaag accctgaggt caagttcaac tggtacgtgg acggcgtgga ggtgcataat    1560
gccaagacaa agccgcggga ggagcagtac aacagcacgt accgtgtggt cagcgtcctc    1620
accgtcctgc accaggactg gctgaatggc aaggagtaca gtgcaaggt ctccaacaaa     1680
gccctcccag cccccatcga gaaaaccatc tccaaagcca aggtgggac ccgtggggtg     1740
cgagggccac atggacagag gccggctcgg cccacccttct gccctgagag tgaccgctgt   1800
accaacctct gtccctacag ggcagccccg agaaccacag gtgtacaccc tgcccccatc   1860
ccgggaggag atgaccaaga accaggtcag cctgacctgc ctggtcaaag gcttctatcc   1920
cagcgacatc gccgtggagt gggagagcaa tgggcagccg gagaacaact acaagaccac   1980
gcctcccgtg ctggactccg acggctcctt cttcctctat agcaagctca ccgtggacaa   2040
gagcaggtgg cagcaggga acgtcttctc atgctccgtg atgcatgagg ctctgcacaa    2100
ccactacacg cagaagagcc tctccctgtc cccgggtaaa tga                     2143
```

<210> SEQ ID NO 9
<211> LENGTH: 1295
<212> TYPE: DNA
<213> ORGANISM: Artificial Sequence
<220> FEATURE:
<223> OTHER INFORMATION: Truncated heavy chain of anti-vitronectin IgG1
      with His-tag sequence

<400> SEQUENCE: 9

```
atggcatgcc ctggcttcct gtgggcactt gtgatctcca cctgtcttga attttccatg     60
gccgaggtgc agctggtgga gtctggggga ggcttggtac agcctggggg gtccctgaga    120
ctctcctgtg cagcctctgg attcaccttt agcagctatg ccatgagctg ggtccgccag    180
gctccaggga aggggctgga gtgggtctca gctattagtg gcagtggtgg tagcacatac    240
tacgcagact ccgtgaaggg ccggttcacc atctccagag acaattccaa gaacacgctg    300
tatctgcaaa tgaacagcct gagggccgag gacacggccg tgtattactg tgcaagagac    360
gaccggccta gggagttgga ctcctggggc caaggtaccc tggtcaccgt ctcgacaggt    420
gagtgcggcc gcgagcccag acactggacg ctgaacctcg cggacagtta agaacccagg    480
ggcctctgcg ccctgggccc agctctgtcc cacaccgcgg tcacatggca ccacctctct    540
tgcagcctcc accaagggcc catcggtctt ccccctggca ccctcctcca agagcacctc    600
tgggggcaca gcggccctgg gctgcctggt caaggactac ttccccgaac cggtgacggt    660
gtcgtggaac tcaggcgccc tgaccagcgg cgtgcacacc ttcccggctg tcctacagtc    720
ctcaggactc tactccctca gcagcgtggt gaccgtgccc tccagcagct tgggcaccca    780
gacctacatc tgcaacgtga atcacaagcc cagcaacacc aaggtggaca gagagttgg    840
tgagaggcca gcacagggag ggagggtgtc tgctggaagc caggctcagc gctcctgcct    900
ggacgcatcc cggctatgca gtcccagtcc agggcagcaa gcaggcccc gtctgcctct    960
tcacccggag gcctctgccc gccccactca tgctcaggga gagggtcttc tggcttttc   1020
cccaggctct gggcaggcac aggctaggtg cccctaaccc aggccctgca cacaaagggg  1080
caggtgctgg gctcagacct gccaagagcc atatccggga ggaccctgcc cctgacctaa  1140
gcccacccca aaggccaaac tctccactcc ctcagctcgg acaccttctc tcctcccaga  1200
ttccagtaac tcccaatctt ctctctgcag agcccaaatc ttgtgacaaa actcacacat  1260
gcccaccgtg cccacatcat caccatcacc attga                             1295
```